(12) United States Patent
Spilker et al.

(10) Patent No.: US 8,147,766 B2
(45) Date of Patent: Apr. 3, 2012

(54) SELECTIVE, INTEGRATED PROCESSING OF BIO-DERIVED ESTER SPECIES TO YIELD LOW MOLECULAR WEIGHT HYDROCARBONS AND HYDROGEN FOR THE PRODUCTION OF BIOFUELS

(75) Inventors: Kerry K. Spilker, Houston, TX (US); Roger Vogel, Fairfield, CA (US); James F. Stevens, Katy, TX (US); Peter C. Ricci, Spring, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/098,968

(22) Filed: May 2, 2011

(65) Prior Publication Data
US 2011/0211998 A1    Sep. 1, 2011

Related U.S. Application Data

(62) Division of application No. 12/330,306, filed on Dec. 8, 2008, now Pat. No. 7,960,598.

(51) Int. Cl.
*B01J 8/00* (2006.01)

(52) U.S. Cl. ........ 422/187; 585/240; 585/241; 585/242; 585/302; 585/303; 585/304; 585/310; 585/733; 560/1; 560/129; 44/385; 44/386; 44/605; 44/606

(58) Field of Classification Search .......... 585/240–242, 585/302–304, 310, 733; 44/385–386, 605–606; 560/1, 129

See application file for complete search history.

(56) References Cited

U.S. PATENT DOCUMENTS

| | | | |
|---|---|---|---|
| 4,859,312 A | 8/1989 | Miller | |
| 4,992,605 A | 2/1991 | Craig et al. | |
| 5,158,665 A | 10/1992 | Miller | |
| 5,300,210 A | 4/1994 | Zones et al. | |
| 2009/0239279 A1* | 9/2009 | Hall et al. | 435/167 |

OTHER PUBLICATIONS

Chen et al., "Catalytic pyrolysis of biomass for hydrogen rich fuel gas production," Energy Conversion & Management, vol. 44, pp. 2289-2296, 2003.
Dry, "The Fischer-Tropsch process: 1950-2000," Catalysis Today, vol. 71, pp. 227-241, 2002.
Huber et al., "Synthesis of Transportation Fuels from Biomass: Chemistry, Catalysts, and Engineering," Chem. Rev., vol. 106, pp. 4044-4098 (2006).
Lappas et al., "Biomass pyrolysis in a circulating fluid bed reactor for the production of fuels and chemicals," Fuel, vol. 81, pp. 2087-2095, 2002.
Marquevich et al., "Steam Reforming of Sunflower Oil for Hydrogen Production," Ind. Eng. Chem. Res., vol. 39, pp. 2140-2147, 2000.
Rana et al., "A Review of Recent Advances on Process Technologies for Upgrading of Heavy Oils and Residua," Fuel, vol. 86, pp. 1216-1231 (2007).
Wang et al., "Biomass to Hydrogen via Fast Pyrolysis and Catalytic Steam Reforming of the Pyrolysis Oil or Its Fractions," Ind. Eng. Chem. Res., vol. 36, pp. 1507-1518, 1997.

* cited by examiner

*Primary Examiner* — Walter D Griffin
*Assistant Examiner* — Brian McCaig
(74) *Attorney, Agent, or Firm* — Edward T. Mickelson

(57) ABSTRACT

The present invention relates to methods and systems for processing biomass to selectively yield a variety of hydrocarbon molecules and hydrogen as products, wherein some or all of these products can be further utilized for other biomass processing sub-processes, particularly wherein they lead to the generation of biofuels and/or other high-value products.

10 Claims, 2 Drawing Sheets

US 8,147,766 B2

SELECTIVE, INTEGRATED PROCESSING OF BIO-DERIVED ESTER SPECIES TO YIELD LOW MOLECULAR WEIGHT HYDROCARBONS AND HYDROGEN FOR THE PRODUCTION OF BIOFUELS

CROSS-REFERENCE TO RELATED APPLICATIONS

This application for patent is a Divisional of U.S. patent application Ser. No. 12/330,306, now U.S. Pat. No. 7,960,598, filed Dec. 8, 2008.

FIELD OF THE INVENTION

The present invention relates to methods and systems for processing biomass to selectively yield a variety of hydrocarbon molecules and hydrogen as products, wherein some or all of these products can be further utilized for other biomass processing sub-processes, particularly wherein they lead to the generation of biofuels and/or other high-value products.

BACKGROUND

Many methods have been suggested for utilizing biofuel for energy production in order to compensate for at least a portion of the fossil fuel currently used in such energy production, and thereby also decrease net $CO_2$ emissions in the overall energy production cycle. See, e.g., Huber et al., "Synthesis of Transportation Fuels from Biomass: Chemistry, Catalysts, and Engineering," Chem. Rev., vol. 106, pp. 4044-4098, 2006.

Unfortunately, biofeedstocks are generally considered to be low energy fuels, and not easily utilized for energy production. The low energy content of biomass renders it generally inadequate for high-efficiency production of energy, such as high-temperature, high-pressure steam or electricity. Additionally, non-uniformity in the raw material (i.e., biomass), differences in its quality, and other similar hard-to-control variations, may cause problems in an energy production cycle that relies heavily on such fuel.

In view of the foregoing, methods and/or systems for enhancing and/or integrating a variety of biofuel synthesis routes with each other, and/or with traditional refinery processes, would be extremely useful—particularly wherein they can provide dynamic adaptability in terms of their ability to accommodate change in either or both of their feedstock material and their product stream(s).

BRIEF DESCRIPTION OF THE INVENTION

So as to address at least some of the above-described limitations and/or recognized needs of biofuels and/or their processing, in some embodiments the present invention is directed to methods (i.e., processes) and systems by which various biomass feedstock processing routes can be integrated with each other and/or with other conventional refinery processes. Advantages of such integration include, but are not limited to, dynamic adaptability. Dynamic adaptability affords the ability to rapidly react to changes/variability in the feedstocks and/or product streams, whether such change/variation is desired or not.

In some embodiments, the present invention is directed to one or more methods comprising the steps of: (a) treating a triglyceride-containing biomass so as to yield a triglyceride fraction comprising triglycerides and a non-triglyceride fraction; (b) transesterifying a first portion of the triglycerides in the triglyceride fraction to yield monoesters; (c) steam-reforming a second portion of the triglycerides in the triglyceride fraction to yield bio-derived $H_2$; (d) hydroprocessing at least a portion of the monoesters with $H_2$ in a hydroprocessing reactor to yield one or more hydrocarbon products of a first type, wherein a portion of the $H_2$ so utilized is provided by at least a portion of the bio-derived $H_2$; and (e) pyrolyzing at least a portion of the non-triglyceride fraction to yield a pyrolysis oil, at least a portion of which is hydroprocessed in the hydroprocessing reactor to yield one or more hydrocarbon products of a second type.

In some or other embodiments, the present invention is directed to one or more systems for implementing the above-mentioned methods, said systems comprising: (a) an extraction unit for treating a triglyceride-containing biomass so as to yield a triglyceride fraction comprising triglycerides and a non-triglyceride fraction; (b) a transesterification unit for transesterifying a first portion of the triglycerides in the triglyceride fraction to yield monoesters; (c) a steam-reforming unit for converting a second portion of the triglycerides in the triglyceride fraction into bio-derived $H_2$; (d) a hydroprocessing reactor for hydroprocessing at least a portion of the monoesters with $H_2$ to yield one or more hydrocarbon products of a first type, wherein a portion of the $H_2$ so utilized is provided by the bio-derived $H_2$; and (e) a pyrolysis unit operable for pyrolyzing at least a portion of the non-triglyceride fraction to pyrolysis oil, at least a portion of which is hydroprocessed in the hydroprocessing reactor to yield one or more hydrocarbon products of a second type.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

1. Introduction

Figure 1:
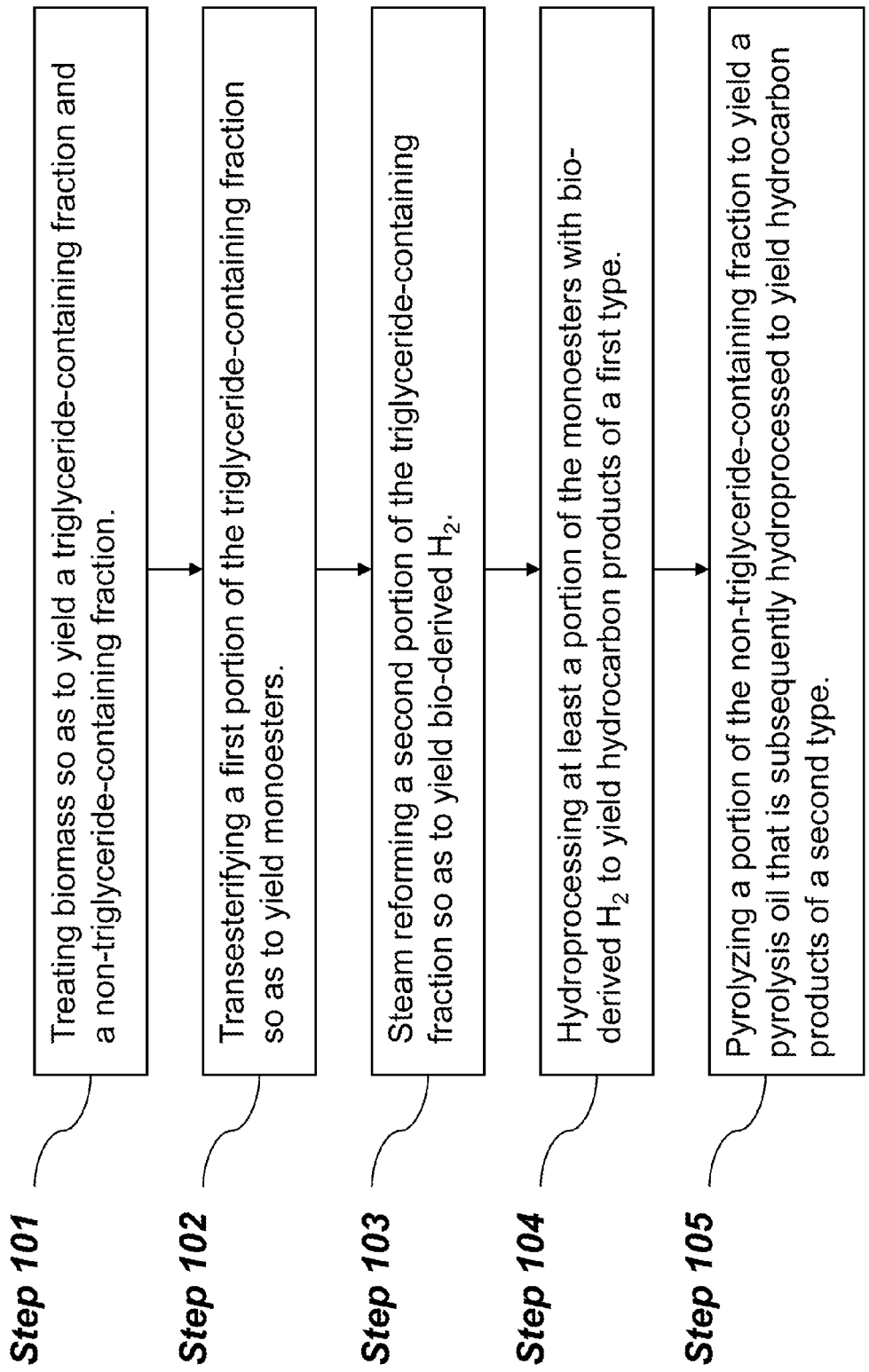
FIG. 1 illustrates, in flow diagram form, methods for integrating biomass processing routes, in accordance with some embodiments of the present invention.

Embodiments of the present invention are directed, at least in part, to methods (processes) and systems for processing biomass to selectively yield a variety of hydrocarbon molecules and hydrogen as products, wherein some or all of these products can be further utilized for other biomass processing sub-processes via process integration, so as to yield biofuels and/or other high-value products.

A unique aspect of at least some such above-described embodiments of the present invention is the dynamic adaptability such methods and systems derive from various levels of process integration. Because biomass composition is rarely seen as constant, economic large-scale processing of such material for the production of biofuels must be tolerant of variability inherent to biomass feedstocks. Such adaptability and variation tolerance also lends itself to increased flexibility in modulating the output of product and/or intermediate streams, as the need arises.

2. Definitions

Certain terms and phrases are defined throughout this description as they are first used, while certain other terms used in this description are defined below:

The prefix "bio," as used herein, refers to an association with a renewable resource of biological origin, such resources generally being exclusive of fossil fuels.

A "biologically-derived oil," as defined herein, refers to any triglyceride-containing oil that is at least partially derived from a biological source such as, but not limited to, crops, vegetables, microalgae, and the like. Such oils may further comprise free fatty acids. The biological source is henceforth referred to as "biomass." For more on the advantages of using microalgae as a source of triglycerides, see R. Baum, "Microalgae are Possible Source of Biodiesel Fuel," Chem. & Eng. News, vol. 72(14), pp. 28-29, 1994. Herein, the terms "vegetable oil," "crop oil," and "biologically-derived oil" will generally be used interchangeably.

"Triglyceride," as defined herein, refers to the class of molecules having the following molecular structure:

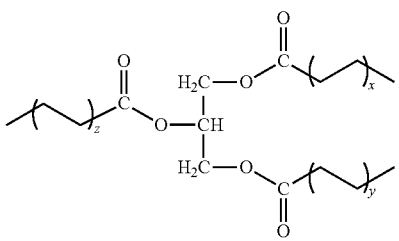

where x, y, and z can be the same or different, and wherein one or more of the branches defined by x, y, and z can have unsaturated regions.

A "triglyceride-containing biomass," as described herein, is any biomass material from which triglyceride species can be extracted.

A "carboxylic acid" or "fatty acid," as defined herein, is a class of organic acids having the general formula:

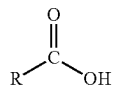

where "R" is generally a saturated (alkyl)hydrocarbon chain or a mono- or polyunsaturated (alkenyl)hydrocarbon chain.

"Lipids," as defined herein, broadly refers to the class of molecules comprising fatty acids, and tri-, di-, and monoglycerides.

"Hydrolysis" of triglycerides yields free fatty acids and glycerol, such fatty acid species also commonly referred to as carboxylic acids (see above).

"Transesterification," or simply "esterification," refers to the reaction between a fatty acid and an alcohol to yield an ester species.

"Hydroprocessing" or "hydrotreating" refers to processes or treatments that react a hydrocarbon-based material with hydrogen, typically under pressure and with a catalyst (hydroprocessing can be non-catalytic). Such processes include, but are not limited to, hydrodeoxygenation (of oxygenated species), hydrotreating, hydrocracking, hydroisomerization, and hydrodewaxing. For examples of such processes, see Cash et al., U.S. Pat. No. 6,630,066; and Elomari, U.S. Pat. No. 6,841,063. Embodiments of the present invention utilize such hydroprocessing to convert triglycerides to paraffins. The terms "hydroprocessing" and "hydrotreating" are used interchangeably herein.

"Isomerizing," as defined herein, refers to catalytic processes that typically convert n-alkanes to branched isomers. ISODEWAXING (Trademark of CHEVRON U.S.A. INC.) catalysts are representative catalysts used in such processes. See, e.g., Zones et al., U.S. Pat. No. 5,300,210; Miller, U.S. Pat. No. 5,158,665; and Miller, U.S. Pat. No. 4,859,312.

"Transportation fuels," as defined herein, refer to hydrocarbon-based fuels suitable for consumption by vehicles. Such fuels include, but are not limited to, diesel, gasoline, jet fuel and the like.

"Diesel fuel," as defined herein, is a material suitable for use in diesel engines and conforming to the current version at least one of the following specifications: ASTM D 975— "Standard Specification for Diesel Fuel Oils"; European Grade CEN 90; Japanese Fuel Standards JIS K 2204; The United States National Conference on Weights and Measures (NCWM) 1997 guidelines for premium diesel fuel; and The United States Engine Manufacturers Association recommended guideline for premium diesel fuel (FQP-1A).

The term "biodiesel," as used herein, refers to diesel fuel that is at least significantly derived from a biological source, and which is generally consistent with ASTM International Standard Test Method D-6751. Often, biodiesel is blended with conventional petroleum diesel. B20 is a blend of 20 percent biodiesel with 80 percent conventional diesel. B100 denotes pure biodiesel.

"Conventional biodiesel," as defined herein, refers to ester-based biodiesel produced via a transesterification of triglyceride-containing vegetable oils.

A "conventional refinery," as defined herein, refers to the infrastructure utilized in the processing of petroleum to yield fuels, lubricants, and/or other petrochemical products.

A "Generation 1 biofuel," as defined herein, is any biofuel whose production adversely impacts the food chain.

A "Generation 2 biofuel," as defined herein, is any biofuel whose production is independent of the food chain.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551, and D 5771.

As defined herein, "$C_n$," where "n" is an integer, describes a hydrocarbon or hydrocarbon-containing molecule or fragment (e.g., an alkyl or alkenyl group) wherein "n" denotes the number of carbon atoms in the fragment or molecule—irrespective of linearity or branching.

"Dynamic adaptability," as defined herein, refers to an inherent ability to accommodate changes in feedstock composition and/or desired intermediate and/or product output.

3. Methods

As mentioned previously, and with reference to FIG. 1, in some embodiments the present invention is directed to one or more methods for integrating biomass processing so as to afford dynamic adaptability in the production of biofuels and/or other bio-derived products, such methods comprising the steps of: (Step 101) treating a triglyceride-containing biomass (Biomass I) so as to yield a triglyceride fraction comprising triglycerides and a non-triglyceride fraction;

(Step 102) transesterifying a first portion of the triglycerides in the triglyceride fraction to yield monoesters; (Step 103) steam-reforming a second portion of the triglycerides in the triglyceride fraction to yield bio-derived $H_2$; (Step 104) hydroprocessing at least a portion of the monoesters with $H_2$ in a hydroprocessing reactor to yield one or more hydrocarbon products of a first type, wherein a portion of the $H_2$ so utilized is provided by at least a portion of the bio-derived $H_2$; and (Step 105) pyrolyzing at least a portion of the non-triglyceride fraction (optionally with a Biomass II) to yield a pyrolysis oil, at least a portion of which is hydroprocessed in the hydroprocessing reactor to yield one or more hydrocarbon products of a second type.

In some such above-described method embodiments, triglyceride-containing biomass (Biomass I, or biomass of a first type) typically is, or comprises, a vegetable oil that originates from a biomass source selected from the group consisting of crops, vegetables, microalgae, and combinations thereof. Accordingly, the term "vegetable oil" is actually quite broad and can generally be extended to include any biologically-derived oil (vide supra). Those of skill in the art will recognize that generally any biological source of lipids can serve as a source of biomass of a first type from which a biologically-derived oil (e.g., vegetable oil) comprising triglycerides can be obtained. It will be further appreciated that some such sources are more economical and more amenable to regional cultivation, and also that those sources from which food is not derived may be additionally attractive (so as not to be seen as competing with food). Exemplary vegetable oils/oil sources include, but are not limited to, canola, soy, rapeseed, palm, peanut, jatropha, yellow grease, algae, and the like. Biomass containing triglycerides is referred to herein as "triglyceride-containing biomass."

In some such above-described method embodiments, Biomass II (biomass of a second type) can be generally of the same type as Biomass I, and/or it can be different. In the latter case, it can be triglyceride-containing, cellulosic and/or lignocellulosic (e.g., wood). For a review of biomass and its associated processing, see Huber et al., "Synthesis of Transportation Fuels from Biomass: Chemistry, Catalysts, and Engineering," Chem. Rev., vol. 106, pp. 4044-4098, 2006. Note that in some embodiments, the Biomass II further comprises waste plastic and/or other forms of municipal solid waste (MSW).

In some such above-described method embodiments, the biomass (Biomass I or II) undergoes some sort of pretreatment. Processing and/or preprocessing of biomass can include, for example, cultivating, harvesting, mechanical grinding, pelletization, extraction, fermentation, separation, hydrolysis, and any combination of such techniques, wherein such techniques are generally described in Huber. Those of skill in the art will appreciate that variations on such above-described preprocessing techniques can be applied as various needs arise.

In some embodiments, when cellulosic/lignocellulosic biomass is used, methods can benefit from cryogenic processing, wherein cryogenic temperatures (e.g., liquid $N_2$) are used to facilitate the crushing of such fiber-based biomass, leading to improvements in the hydrolysis of such cellulose and hemicellulose. This will be described more fully by way of example (vide infra).

In some above-described method embodiments, the step of pyrolyzing involves a co-pyrolysis of the non-triglyceride fraction with a secondary biomass (i.e., Biomass II). Such pyrolysis techniques are known in the art and can be used and/or adapted for a variety of feeds. See, e.g., Lappas et al., "Biomass pyrolysis in a circulating fluid bed reactor for the production of fuels and chemicals," Fuel, vol. 81, pp. 2087-2095, 2002; and Chen et al., "Catalytic pyrolysis of biomass for hydrogen rich fuel gas production," Energy Conversion & Management, vol. 44, pp. 2289-2296, 2003.

In some above-described method embodiments, a portion of the monoesters are steam-reformed with the triglycerides to yield bio-derived $H_2$ (and CO). Steam-reforming of biomass is known in the art, see, e.g., Wang et al., "Biomass to Hydrogen via Fast Pyrolysis and Catalytic Steam Reforming of the Pyrolysis Oil or Its Fractions," Ind. Eng. Chem. Res., vol. 36, pp. 1507-1518, 1997; and Marquevich et al., "Steam Reforming of Sunflower Oil for Hydrogen Production," Ind. Eng. Chem. Res., vol. 39, pp. 2140-2147, 2000.

In some such above-described method embodiments, the bio-derived $H_2$ is stripped of CO prior to it being introduced into the hydroprocessing reactor. In some or other such above-described method embodiments, at least some of the bio-derived $H_2$, as syngas, is used to make products via Fischer-Tropsch (FT) synthesis. Naturally, for FT synthesis, some or all of the CO could be retained. For a review of Ficher-Tropsch synthesis, see Dry, "The Fischer-Tropsch process: 1950-2000," Catalysis Today, vol. 71, pp. 227-241, 2002.

In some such above-described method embodiments, the step of hydroprocessing involves a hydroprocessing/hydrotreating catalyst and a hydrogen-containing environment. For a general review of hydroprocessing/hydrotreating, see, e.g., Rana et al., "A Review of Recent Advances on Process Technologies for Upgrading of Heavy Oils and Residua," Fuel, vol. 86, pp. 1216-1231, 2007. For an example of how triglycerides can be hydroprocessed to yield a paraffinic product, see, e.g., Craig et al., U.S. Pat. No. 4,992,605.

In some such above-described method embodiments, the step of hydroprocessing involves or otherwise utilizes a hydrotreating catalyst comprising an active metal or metal-alloy hydrotreating catalyst component that is operationally integrated with a refractory support material. In some such embodiments, the active metal catalyst component is selected from the group consisting of cobalt-molybdenum (Co—Mo) catalyst, nickel-molybdenum (Ni—Mo) catalyst, noble metal catalyst, and combinations thereof. In these or other embodiments, the refractory support material typically comprises a refractory oxide support such as, but not limited to, $Al_2O_3$, $SiO_2$—$Al_2O_3$, and combinations thereof. In some particular embodiments, the hydroprocessing step makes use of an alumina-supported nickel-molybdenum catalyst. Variation on catalyst type can be used to vary the type of hydrocarbon products produced.

In some such above-described method embodiments, the hydroprocessing is carried out at a temperature between 550° F. and 800° F. In some such embodiments, the hydroprocessing is carried out under a $H_2$ partial pressure of between 400 pounds-force per square inch gauge (psig) and 2000 psig. In some or other such embodiments, the hydroprocessing is carried out under a $H_2$ partial pressure of between 500 psig and 1500 psig. As with catalyst type, such conditions can play a deterministic role in what types of hydrocarbon products are produced.

In some above-described method embodiments, intermediate divergent pathways afford dynamic process adaptability. In some or other such above-described method embodiments, intermediate product output from the multiple intermediate product streams is amenable to dynamic variation. In some presently-contemplated embodiments, at least some of the intermediate product stream(s) are directed (physically) to one or more process steps for producing one or more additional and/or alternative product species.

In some such above-described method embodiments, the one or more hydrocarbon products of the first and second type are independently selected from the group consisting of Generation 1 biofuels, Generation 2 biofuels, biolubricants, biologically-derived petrochemicals, and combinations thereof.

In some such above-described method embodiments, one or more hydrocarbon products of the first and/or second type are a transportation fuel. Such transportation fuels include, but are not limited to, gasoline, jet fuel, E85, diesel fuel, and the like. Generally, such transportation fuels possess a pour point and cloud point rendering them acceptable for use in specific vehicles, wherein a government regulatory agency and/or a standards organization establishes the acceptable thresholds and/or ranges for such properties. In some or other such above-described method embodiments, one or more hydrocarbon products of the first and/or second type are blended with other fuels of a biological and/or petrochemical origin.

In some such above-described method embodiments, the biologically-derived petrochemicals are selected from the group consisting of esters, organic acids, alcohols, alkenes, alkanes, and combinations thereof. The specific type and molecular weight of such species can be tailored to meet current or anticipated demands. For example, production of straight chain $C_5$ alkanes might yield to the production of branched $C_{16}$ alkanes.

In some such above-described method embodiments, the one or more hydrocarbon products of the first and second type are provided via multiple product streams. In some such embodiments, one or more of such product streams can be further directed to subsequent processing/treatment, wherein some such streams provide precursors and/or intermediates for further processing/treatment.

In some such above-described embodiments, one or more of the hydrocarbon product streams (or fractional streams thereof) are subjected to an additional step of isomerizing, i.e., isomerization. Typically, such isomerization is carried out using an isomerization catalyst. Such isomerization catalysts have traditionally comprised Pt or Pd on a support such as SAPO-11, SM-3, SSZ-32, ZSM-23, ZSM-22, and similar such supports; and/or on an acidic support material such as beta or zeolite Y molecular sieves, $SiO_2$, $Al_2O_3$, $SiO2$-$Al_2O_3$, and combinations thereof. Traditionally, the isomerization is carried out at a temperature between about 500° F. and about 750° F. The operating pressure is typically 200 to 2000 psig, and more typically 200 psig to 1000 psig. Hydrogen flow rate is typically 50 to 5000 standard cubic feet/barrel (SCF/barrel). For other suitable isomerization catalysts, see, e.g., Zones et al., U.S. Pat. No. 5,300,210; Miller, U.S. Pat. No. 5,158,665; and Miller, U.S. Pat. No. 4,859,312.

4. Systems

Figure 2:
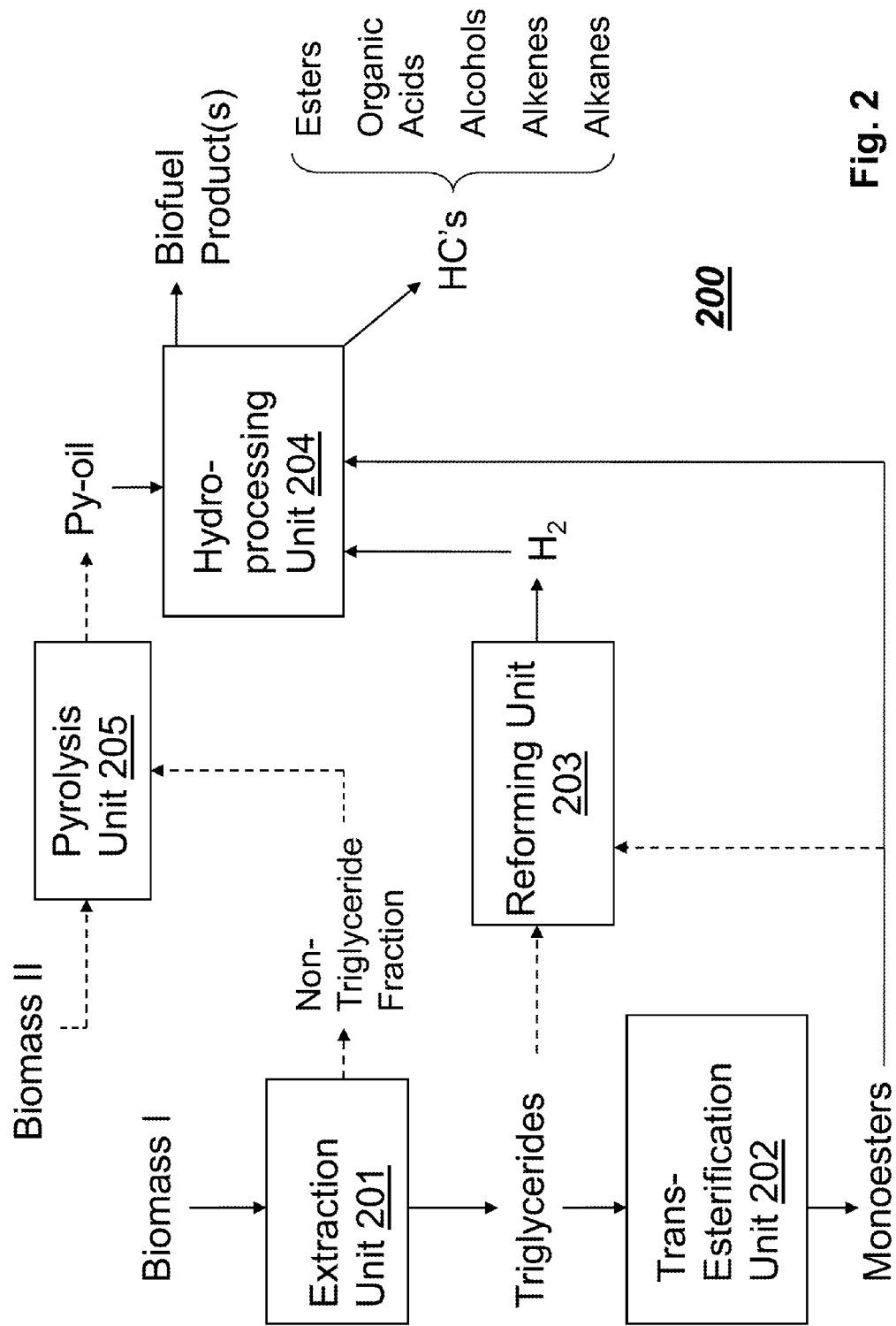
FIG. 2 depicts, schematically, systems for implementing methods such as illustrated in FIG. 1, in accordance with some embodiments of the present invention.

As already mentioned in a previous section, and with reference to FIG. 2, in some embodiments the present invention is directed to one or more systems 200 for implementing the above-described methods, such systems comprising: an extraction unit 201 for treating a triglyceride-containing biomass so as to yield a triglyceride fraction comprising triglycerides and a non-triglyceride fraction; a transesterification unit 202 for transesterifying a first portion of the triglycerides in the triglyceride fraction to yield monoesters; a steam-reforming unit 203 for converting a second portion of the triglycerides in the triglyceride fraction into bio-derived $H_2$; a hydroprocessing reactor 204 for hydroprocessing at least a portion of the monoesters with $H_2$ to yield one or more hydrocarbon products of a first type, wherein a portion of the $H_2$ so utilized is provided by the bio-derived $H_2$; and a pyrolysis unit 205 operable for pyrolyzing at least a portion of the non-triglyceride fraction to pyrolysis oil, at least a portion of which is hydroprocessed in the hydroprocessing reactor to yield one or more hydrocarbon products of a second type.

In some such above-described system embodiments, pyrolysis unit 205 is further operable for co-pyrolyzing the non-triglyceride fraction with a secondary biomass, wherein the secondary biomass is selected from the group consisting of triglyceride-containing biomass, lignocellulosic biomass, cellulosic biomass, and combinations thereof.

In some such above-described system embodiments, the steam-reforming unit 203 is operable for co-reforming a portion of the monoesters with the triglycerides to yield bio-derived $H_2$, wherein said co-reforming is done either sequentially or in parallel.

In some above-described system embodiments, the system is configured such that intermediate divergent pathways afford dynamic process adaptability. Such dynamic process adaptability affords an ability to react "on-the-fly" to input variations and/or changes in product amount or type. Such flexibility enhances the overall economics of such processing.

In some above-described system embodiments, the system further comprises a stripping unit for stripping CO from the bio-derived $H_2$. Alternatively, wherein some or all of the $H_2$ is utilized for Fischer-Tropsch synthesis (e.g., in a Fischer-Tropsch unit), some or all of the CO can be retained such that $H_2$+CO, in appropriate ratios, can be utilized as syngas. Such additional Fischer-Tropsch process(es) can provide for fuel and/or chemical products.

In some such above-described system embodiments, the hydroprocessing unit 204 utilizes a catalyst selected from the group consisting of Co—Mo alloys, Ni—Mo alloys, noble metals, and combinations thereof. Those of skill in the art will recognize that other hydroprocessing catalysts could be similarly used, and that any such catalysts may further employ a refractory support such as, but not limited to, $Al_2O_3$, $SiO_2$—$Al_2O_3$, and the like.

In some such above-described system embodiments, the one or more hydrocarbon products of the first and second type generated by said system are independently selected from the group consisting of Generation 1 biofuels, Generation 2 biofuels, biolubricants, biologically-derived petrochemicals, and combinations thereof.

In some such above-described system embodiments, the one or more hydrocarbon products of the first and second type generated by said system are provided via multiple product streams. As in the case of the intermediate divergent pathways (vide supra), in some such embodiments, the system(s) is configured such that product output from the multiple product streams is amenable to dynamic variation, with similar results and advantages.

In some above-described system embodiments, such systems further comprise one or more biomass preprocessing units, wherein such units can serve to homogenize or otherwise facilitate the further processing of the biomass. An exemplary such preprocessing unit would be one that cryogenically treats lignocellulosic material for enhanced hydrolysis (see Example 1).

In some above-described system embodiments, such systems further comprise an isomerization unit that can subsequently treat any of the product streams (as a whole or in part) so as to dewax or otherwise isomerizes any such stream as deemed necessary.

Generally, all of the above-described system units are configured for selectively-integrating the processing of bio-derived ester species with the production of biofuels, in accordance with the methods described in Section 3. Further, there is typically a proximal relationship between the various units that comprise system 200, but this need not always be the case. Such relationships may be variously influenced by existing infrastructure and other economic considerations.

5. Variations

In addition to the above-described embodiments, in some variously-contemplated alternative embodiments the above-described methods and systems are further integrated, wholly or in part, with one or more methods and systems of a conventional refinery. For example, the bio-derived $H_2$ can be used to hydroprocess conventional petroleum in a conventional refinery. In such a scenario, and while making this the primary use of the $H_2$, such bio-derived $H_2$ could easily be diverted to the manufacture of biofuels and/or other bio-derived chemical products.

6. Example

The following example is provided to demonstrate particular embodiments of the present invention. It should be appreciated by those of skill in the art that the methods/systems disclosed in the example which follows merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE

This Example serves to illustrate a cryogenic preprocessing technique for use in some embodiments of the present invention.

For processing of cellulose to glucose (via hydrolysis), the efficiency of such hydrolysis is enhanced by a de-bundling of the associated fibers (thereby increasing surface area), and by a separation of the holocellulose (cellulose+hemicellulose) from lignin (when the biomass is a lignocellulosic material). Accordingly, the inventors have developed a method by which cellulosic/lignocellulosic fibers are cryogenically treated with liquid $N_2$ (LN2) during a mechanical grinding process. As a result, hydrolysis conditions were milder (reduced residence time, lower temperatures) and used less acid.

7. Conclusion

In summary, the present invention provides for methods and systems for processing biomass to selectively yield a variety of hydrocarbon molecules and hydrogen as products, wherein some or all of these products can be further utilized for other biomass processing sub-processes, particularly wherein they lead to the generation of biofuels and/or other high-value products. The selective process integration and resulting dynamic adaptability offer significant advantages over the existing art.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:

1. A system for generating a hybrid diesel fuel product, said system comprising:
 a) an extraction unit for treating a triglyceride-containing biomass so as to yield a triglyceride fraction comprising triglycerides and a non-triglyceride fraction;
 b) a transesterification unit for transesterifying a first portion of the triglycerides in the triglyceride fraction to yield monoesters;
 c) a steam-reforming unit for converting a second portion of the triglycerides in the triglyceride fraction into bio-derived $H_2$;
 d) a hydroprocessing reactor for hydroprocessing at least a portion of the monoesters with $H_2$ to yield one or more hydrocarbon products of a first type, wherein a portion of the $H_2$ so utilized is provided by the bio-derived $H_2$; and
 e) a pyrolysis unit operable for pyrolyzing at least a portion of the non-triglyceride fraction to pyrolysis oil, at least a portion of which is hydroprocessed in the hydroprocessing reactor to yield one or more hydrocarbon products of a second type.

2. The system of claim 1, wherein the pyrolysis unit is further operable for co-pyrolyzing the non-triglyceride fraction with a secondary biomass, wherein the secondary biomass is selected from the group consisting of triglyceride-containing biomass, lignocellulosic biomass, cellulosic biomass, and combinations thereof.

3. The system of claim 1, wherein the steam-reforming unit is operable for co-reforming a portion of the monoesters with the triglycerides to yield bio-derived $H_2$, and wherein said co-reforming is done either sequentially or in parallel.

4. The system of claim 1, wherein said system is configured such that intermediate divergent pathways afford dynamic process adaptability.

5. The system of claim 1, further comprising a stripping unit for stripping CO from the bio-derived $H_2$.

6. The system of claim 1, wherein the hydroprocessing unit utilizes a catalyst selected from the group consisting of Co—Mo, Ni—Mo, noble metals, and combinations thereof.

7. The system of claim 1, further comprising a Fischer-Tropsch unit that utilizes at least some of the bio-derived $H_2$.

8. The system of claim 1, wherein the one or more hydrocarbon products of the first and second type generated by said system are independently selected from the group consisting of Generation 1 biofuels, Generation 2 biofuels, biolubricants, biologically-derived petrochemicals, and combinations thereof.

9. The system of claim 1, wherein the one or more hydrocarbon products of the first and second type generated by said system are provided via multiple product streams.

10. The system of claim 9, configured such that product output from the multiple product streams is amenable to dynamic variation.

* * * * *